US008173705B2

(12) United States Patent
Tsunenaga et al.

(10) Patent No.: US 8,173,705 B2
(45) Date of Patent: May 8, 2012

(54) AGENT FOR ALLEVIATING WRINKLES (75) Inventors: Makoto Tsunenaga, Yokohama (JP);
Mikiko Kaminuma, Yokohama (JP);
Masaru Suetsugu, Yokohama (JP);
Chika Katagiri, Yokohama (JP)

(73) Assignee: Shiseido Company Ltd., Chuo-ku, Tokyo (JP)

( * ) Notice: Subject to any disclaimer, the term of this patent is extended or adjusted under 35 U.S.C. 154(b) by 132 days.

(21) Appl. No.: 12/530,841

(22) PCT Filed: Mar. 14, 2008

(86) PCT No.: PCT/JP2008/054765
§ 371 (c)(1),
(2), (4) Date: Sep. 11, 2009

(87) PCT Pub. No.: WO2008/114732
PCT Pub. Date: Sep. 25, 2008

(65) Prior Publication Data
US 2010/0113450 A1 May 6, 2010

(30) Foreign Application Priority Data
Mar. 16, 2007 (JP) ................................. 2007-069134

(51) Int. Cl.
*A61K 31/195* (2006.01)
(52) U.S. Cl. .................... 514/567; 514/561; 514/562
(58) Field of Classification Search .................... None
See application file for complete search history.

(56) References Cited

U.S. PATENT DOCUMENTS

| 4,016,287 A | 4/1977 | Eberhardt et al. |
| 5,939,078 A | 8/1999 | Fjimura et al. |
| 2004/0044077 A1 | 3/2004 | Katagiri et al. |

FOREIGN PATENT DOCUMENTS

| JP | 51-148041 | 12/1976 |
| JP | 2005-239609 | 9/2005 |
| JP | 2005-239645 | 9/2005 |
| JP | 2006-298796 | 11/2006 |
| WO | 03/053466 | 7/2003 |

OTHER PUBLICATIONS

Health Encyclopedia_Wrinkles ( 2011).*
Discovery Health "How to Prevent Wrinkles" (2010).*
MedicineNet.com, Wrinkles-causes and treatment (2005).*
JP2005-239609 English Translation (2005).*
Kligman et al., "The anatomy and pathogenesis of wrinkles," British Journal of Dermatology (1985) 113, pp. 37-42.
Matsunaga et al., "Establishment of a mouse skin model of the lichenification in human chronic eczematous dermatitis," British Journal of Dermatology 2007 156, pp. 884-891.
Katagiri et al., "Serpin squamous cell carcinoma antigen inhibits UV-induced apoptosis via suppression of c-JUN NH2-terminal kinase," The Journal of Cell Biology, vol. 172, No. 7, Mar. 27, 2006, pp. 983-990.
Makiura et al., "Atopic Dermatitis-like Symptoms in HR-1 Hairless Mice Fed a Diet Low in Magnesium and Zinc," The Journal of International Medical Research 2004, 32, pp. 392-399.
Kligman, "The ultraviolet-irradiated hairless mouse: A model for photoaging," Journal of the American Academy of Dermatology 1989, vol. 21, pp. 623-631.
Imokawa et al., "Analysis of etiologic factors involved in stratum corneum function in fine wrinkle formation and its prevention," Fragrance Journal 1992, vol. 11, pp. 29-42.
International Search Report for corresponding PCT/JP2008/054765 mailed Apr. 8, 2008, four pages.

* cited by examiner

*Primary Examiner* — James D Anderson
*Assistant Examiner* — Bong-Sook Baek
(74) *Attorney, Agent, or Firm* — Rankin, Hill & Clark LLP (57) ABSTRACT The present invention provides an agent for preventing and alleviating wrinkles which has excellent effects of preventing and alleviating wrinkles formed by decreased barrier function of the skin owing to aging or photo aging, that is graphic wrinkles or linear wrinkles. The agent for preventing and alleviating wrinkles consisting of one or more compounds selected from the group consisting of gamma-aminobutyric acid derivatives represented by the following formula (1) or N,N,N-trimethyl gamma-aminobutyric acid represented by the following formula (3) and salts thereof:

$$R_2\text{-}N(R_1)\text{-}CH_2\text{-}CH_2\text{-}CH_2\text{-}COOH \quad (1)$$

$$X_1, X_2, X_3\text{-aryl-}(CH_2)_n\text{-}Y \quad (2)$$

$$(CH_3)_3N^+\text{-}CH_2\text{-}CH_2\text{-}CH_2\text{-}COOH \quad (3)$$

wherein $R_1$ and $R_2$ independently represent any of a hydrogen atom, an alkyl group having 1 to 3 carbon atoms, a benzyloxycarbonyl group, a cyclohexyl group, a cyclohexanemethyl group, a cyclohexanecarbonyl group, a guanidino group formed with nitrogen atom in the formula (1), an ureido group formed with nitrogen atom in the formula (1), and a group represented by following formula (2). Additionally, $R_1$ and $R_2$ may jointly form a piperidine ring, morpholine ring, or pyrrolidine ring. Both of $R_1$ and $R_2$ are not simultaneously a hydrogen atom.

4 Claims, 1 Drawing Sheet

SEQUENCE LISTING

<160> NUMBER OF SEQ ID NOS: 4

<210> SEQ ID NO 1
<211> LENGTH: 17
<212> TYPE: DNA
<213> ORGANISM: Artificial
<220> FEATURE:
<223> OTHER INFORMATION: Forward Primer

```
<400> SEQUENCE: 1
gtgctatctg gagtcct                                              17

<210> SEQ ID NO 2
<211> LENGTH: 16
<212> TYPE: DNA
<213> ORGANISM: Artificial
<220> FEATURE:
<223> OTHER INFORMATION: Reverse Primer

<400> SEQUENCE: 2
ctgttgttgc cagcaa                                               16

<210> SEQ ID NO 3
<211> LENGTH: 19
<212> TYPE: DNA
<213> ORGANISM: Artificial
<220> FEATURE:
<223> OTHER INFORMATION: Forward Primer

<400> SEQUENCE: 3
gaaggtgaag gtcggagtc                                            19

<210> SEQ ID NO 4
<211> LENGTH: 20
<212> TYPE: DNA
<213> ORGANISM: Artificial
<220> FEATURE:
<223> OTHER INFORMATION: Reverse Primer

<400> SEQUENCE: 4
gaagatggtg atgggatttc                                           20
```

AGENT FOR ALLEVIATING WRINKLES

RELATED APPLICATIONS

The present application is a U.S. national stage of PCT/JP2008/054765 filed on Mar. 14, 2008. This application claims the priority of Japanese Patent Application No. 2007-69134 filed on Mar. 16, 2007, which is incorporated herein by reference. The application includes a sequence listing, which is hereby incorporated by reference, that complies with the American Standard Code for Information Interchange (ASCII) and can be viewed using an IBM-PC compatible computer using the MS-Windows operating system.

FIELD OF THE INVENTION

The present invention relates to an agent for preventing and alleviating wrinkles, which has effects of preventing wrinkle formation and alleviating formed wrinkles.

BACKGROUND OF THE INVENTION

Aging proceeds in all organs of the entire body. In the observable skin, especially in the facial surface on which people tend to focus attention, wrinkles and fine wrinkles formed with advancing age are annoying many middle-aged and older people, especially women, all over the world. Conventionally, there has been demand for cosmetics for alleviating wrinkles, however, the mechanism regarding aging and wrinkles has not been largely clarified. Hence, in the conventional cosmetics, moisturizers such as glycerin, biochemical products such as mucopolysaccharides and collagen, and synthetic polymer products have been blended merely to keep moisture of the skin for alleviating wrinkles.

The method of classifying wrinkles into three groups (i.e. a graphic wrinkle, a crinkle, and a linear wrinkle) on the basis of distinction in appearance is known (refer to Non-patent literature 1). The moisturizing function of the aforementioned components contained in the conventional cosmetics is effective only for limited crinkles, that is the wrinkles owing to dryness, formed by rapidly losing water. A graphic wrinkle is a deep and crisscross wrinkle formed in the skin of exposed area such as facial surface and neck, and sunlight gives a considerable effect on the graphic wrinkle. A cutaneous change, as represented by a wrinkle induced by sunlight, is called "photo aging". For photo aging, the method of irradiating UVB on the back of a hairless mouse, proposed by Kligman et. al., has been established as a method using an animal model (refer to Non-patent literature 2). For details, by initially irradiating the back of hairless mouse (e.g. HR-1 or skh-1) with a low irradiance of UVB (290 to 320 nm wavelength) and gradually increasing the irradiance level to irradiate it with 4 J or more UVB in total for 10 weeks or more, the barrier function of the stratum corneum is decreased and a deep wrinkle which is perpendicular to the midline is induced.

Linear wrinkles, also called expression wrinkles, are so-called "crow's feet" in the outer corner of one's eye or fine wrinkles formed in an area which is constantly moved, such as around mouth or between the eyebrows. The linear wrinkle becomes prominent in their thirties or later. This kind of wrinkle is formed by skin deformation owing to facial expressions, and it may be formed even at an early age depending on a frequency of such deformation. However, the decreased barrier function of the stratum corneum, caused as a result of repeated drying of the skin, is known as a major factor that the linear wrinkle becomes apparent (refer to Non-patent literature 3).

It is difficult to alleviate a graphic wrinkle or a linear wrinkle by applying mere moisturizers, and decreased barrier function of the skin gives an affect on these wrinkles as a wrinkle formation factor. Wrinkles can be formed on the back of a mouse by repeatedly damaging the skin barrier on the back of the mouse by tape-stripping (refer to Non-patent literature 4). In a hairless mouse having atopic-like skin, which is developed as a model for decreased barrier function of the skin, dryness in the skin and formation of wrinkles were observed (refer to Non-patent literature 5).

As described above, there is a close relation between decreased barrier function of the skin and formation of graphic wrinkle or linear wrinkle. Normal growth and appropriate differentiation of epidermal keratinocytes are important for barrier function of the skin. It is known that, for atopic dermatitis which has abnormal growth and differentiation of epidermic cells, squamous cell carcinoma antigen (hereinafter mentioned as SCCA) is increased abnormally (refer to Patent Literature 1). Additionally, it is known that UV irradiation makes growth and differentiation of epidermic cell abnormal and increase the SCCA expression. For example, it is reported that, for human, the facial skin having wrinkles owing to constant exposure to sunlight has higher SCCA expression compared with the body skin having no exposure to sunlight (refer to Patent literatures 1 and 2).

Non-patent literature 1: Kligman A M, Br. J. Dermatol. 113: 37-42 (1985).
Non-patent literature 2: Kligman L H et al., J. Am. Acad. Dermatol. 21:623-631 (1989). Non-patent literature 3: Imokawa G., et al. Fragance Journal, 20(11); 29-42 (1992). Non-patent literature 4: Matsunaga M, British J. dermatol., 156 (5); 884-891 (2007). Non-patent literature 5: Makiura M et al., J Int Med. Res. 32:392-399 (2004), Non-patent literature 6: Katagiri C., J. C. B., 172(7); 983-990 (2006). Patent literature 1: WO2006/098523. Patent literature 2: Japanese Unexamined Patent Publication 2005-27343

DISCLOSURE OF THE INVENTION

Problem to be Solved by the Invention

The present invention has been made in view of the aforementioned problems, and an object of the invention is to provide an agent for preventing and alleviating wrinkles, which has excellent effects of preventing and alleviating wrinkles which cannot be alleviated only by moisturizing effect and are formed by decreased barrier function of the skin owing to aging or photo aging, that is, graphic wrinkles or linear wrinkles.

Means to Solve the Problem

To solve the aforementioned problems, the present inventors have diligently studied and found that gamma-aminobutyric acid derivatives and salts thereof prevent decreased barrier function of the skin by inhibiting epidermal SCCA expression. Accordingly, the present inventors have found that the gamma-aminobutyric acid derivatives and salts thereof are the compounds having an excellent effect of alleviating graphic wrinkles or linear wrinkles which are formed by decreased barrier function of the skin owing to aging or photo aging and an excellent effect of preventing formation thereof. Thus the present invention has been accomplished.

The present invention provides an agent for preventing and alleviating wrinkles consisting of one or more compounds selected from the group consisting of gamma-aminobutyric acid derivatives represented by following formula (1) or (3) and salts thereof:

wherein $R_1$ and $R_2$ independently represent any of a hydrogen atom, an alkyl group having 1 to 3 carbon atoms, a benzyloxycarbonyl group, a cyclohexyl group, a cyclohexanemethyl group, a cyclohexanecarbonyl group, a guanidino group formed with nitrogen atom in the formula (1), an ureido group formed with nitrogen atom in the formula (1), and a group represented by following formula (2). Additionally, $R_1$ and $R_2$ may jointly form a piperidine ring, morpholine ring, or pyrrolidine ring. Both of $R_1$ and $R_2$ are not simultaneously a hydrogen atom.

In the formula (2), Y represents any of nil (i.e. non-substitution), a carbonyl group, and a sulfonyl group. The value of n may be 0 or 1, but it is not 1 when Y represents a sulfonyl group. $X_1$, $X_2$, and $X_3$ independently represent any of a hydrogen atom and a methoxy group, but all of $X_1$, $X_2$, and $X_3$ are hydrogen atoms when n is 1.

The formula (3) represents N,N,N-trimethyl gamma-aminobutyric acid.

It is preferred that, in the aforementioned formula (1), any one of $R_1$ and $R_2$ is any of an alkyl group having 1 to 3 carbon atoms, a benzyloxycarbonyl group, a guanidino group formed with nitrogen atom in the formula (1), an ureido group formed with nitrogen atom in the formula (1), a cyclohexyl group, a cyclohexanemethyl group, a cyclohexanecarbonyl group, and a group represented by the formula (2).

It is preferred that the group represented by the formula (2) is a phenyl group, a benzyl group, a benzenesulfonyl group, a benzoyl group, or a phenylacetyl group.

In addition, it is preferred that any one of $R_1$ and $R_2$ is a hydrogen atom or a methyl group.

In addition, it is preferred that, in the aforementioned formula (1), $R_1$ and $R_2$ jointly form a piperidine ring, morpholine ring, or pyrrolidine ring.

It is preferred that the aforementioned formula (1) represents one or more compounds selected from the group consisting of N-methyl gamma-aminobutyric acid, N,N-dimethyl gamma-aminobutyric acid, N-benzyloxycarbonyl gamma-aminobutyric acid, N-cyclohexyl gamma-aminobutyric acid, N-cyclohexyl-N-methyl gamma-aminobutyric acid, N-cyclohexanemethyl gamma-aminobutyric acid, N-cyclohexanemethyl-N-methyl gamma-aminobutyric acid, N-cyclohexanecarbonyl gamma-aminobutyric acid, 4-guanidino butyric acid, 4-ureido butyric acid, N-phenyl gamma-aminobutyric acid, N-phenyl-N-methyl gamma-aminobutyric acid, N-benzyl gamma-aminobutyric acid, N-benzyl-N-methyl gamma-aminobutyric acid, N-benzoyl gamma-aminobutyric acid, N-phenylacetyl gamma-aminobutyric acid, N-benzenesulfonyl gamma-aminobutyric acid, 4-(1'-piperidine) butyric acid, 4-(1'-morpholine) butyric acid, or 4-(1'-pyrrolidine) butyric acid.

Effect of the Invention

According to the present invention, an agent for preventing and alleviating wrinkles which has an excellent effect of alleviating graphic wrinkles or linear wrinkles formed by decreased barrier function of the skin owing to aging or photo aging and an excellent effect of preventing formation of such wrinkles can be provided.

BEST MODE FOR CARRYING OUT THE INVENTION

Best mode for implementing the present invention are explained below.

In the present invention, one or more compounds selected from the group consisting of gamma-aminobutyric acid derivatives represented by the following formula (1) or (3) and salts thereof are used.

In the formula (1), $R_1$ and $R_2$ independently represent any of a hydrogen atom, an alkyl group having 1 to 3 carbon atoms, a benzyloxycarbonyl group, a guanidino group formed with nitrogen atom in the formula (1), an ureido group formed with nitrogen atom in the formula (1), a cyclohexyl group, a cyclohexanemethyl group, a cyclohexanecarbonyl group, and a group represented by the following formula (2). Additionally, $R_1$ and $R_2$ may jointly form a piperidine ring, morpholine ring, or pyrrolidine ring. Both of $R_1$ and $R_2$ are not simultaneously a hydrogen atom.

(2)

In the formula (2), Y represents any of nil (i.e. non-substitution), a carbonyl group, and a sulfonyl group. The value of n may be 0 or 1, but it is not 1 when Y represents a sulfonyl group. $X_1$, $X_2$, and $X_3$ independently represent any of a hydrogen atom and a methoxy group, but all of $X_1$, $X_2$, and $X_3$ are hydrogen atoms when n is 1.

(3)

The formula (3) represents N,N,N-trimethyl gamma-aminobutyric acid. The gamma-aminobutyric acid derivatives of the present invention are represented by the formula (1) or (3). The formula (3) represents N,N,N-trimethyl gamma-aminobutyric acid (i.e. (3-carboxypropyl)trimethyl ammonium).

For the gamma-aminobutyric acid derivatives of the present invention, in the formula (1), $R_1$ and $R_2$ independently represent any of a hydrogen atom, an alkyl group having 1 to 3 carbon atoms, a benzyloxycarbonyl group, a cyclohexyl group, a cyclohexanemethyl group, a cyclohexanecarbonyl group, a guanidino group formed with nitrogen atom in the formula (1), an ureido group formed with nitrogen atom in the formula (1), and a group represented by the following formula (2). Additionally, $R_1$ and $R_2$ may jointly form a piperidine ring, morpholine ring, or pyrrolidine ring. Both of $R_1$ and $R_2$ are not simultaneously a hydrogen atom.

In the formula (1), each of $R_1$ and $R_2$ may be any atom or group so far as it is within the above-mentioned range. It is preferred that any one of $R_1$ and $R_2$ is a hydrogen atom or an alkyl group having 1 to 3 carbon atoms when $R_1$ and $R_2$ don't form piperidine ring, morpholine ring, or pyrrolidine ring because good effects can be achieved. More preferably, any one of $R_1$ and $R_2$ is a hydrogen atom or a methyl group, and most preferably a hydrogen atom.

In the formula (1), when any one of $R_1$ and $R_2$ is a benzyloxycarbonyl group, a cyclohexyl group, a cyclohexanemethyl group, a cyclohexanecarbonyl group, a guanidino group formed with nitrogen atom in the formula (1), or an ureido group formed with nitrogen atom in the formula (1), preferred examples of formula (1) corresponding to the above-mentioned groups include an N-carbobenzyloxy gamma-aminobutyric acid, a cyclohexyl group, a cyclohexanemethyl group, a cyclohexanecarbonyl group, 4-ureido butyric acid, 4-guanidino butyric acid, and N-methyl forms thereof.

When either or both of $R_1$ and $R_2$ is an alkyl group having 1 to 3 carbon atoms, examples of the alkyl group include a methyl group, an ethyl group, an n-propyl group, and an isopropyl group. As mentioned above, a methyl group is preferable among them because good effects of the present invention can be achieved.

Preferred examples of the formula (1) corresponding to the above-mentioned groups include N-methyl gamma-aminobutyric acid and N,N-dimethyl gamma-aminobutyric acid.

In the formula (1), when any one of $R_1$ and $R_2$ represents the aforementioned formula (2), Y in the formula (2) represents any of nil (i.e. non-substitution), a carbonyl group, and a sulfonyl group. The value of n may be 0 or 1, but it is not 1 when Y represents a sulfonyl group. Thus, depending on what kind of a substituent Y represents, the formula (2) represents any of a phenyl group, a benzyl group, a benzoyl group, a phenylacetyl group, and a benzenesulfonyl group, which further depends on what kind of a substituent $X_1$, $X_2$, and $X_3$ independently represent. $X_1$, $X_2$, and $X_3$ independently represent any of a hydrogen atom and a methoxy group. All of $X_1$, $X_2$, and $X_3$ are hydrogen atoms when n is 1.

It is preferred that $X_1$, $X_2$, and $X_3$ are within the above-mentioned range because good effects of the present invention can be achieved, stabilities and physicalities of other components are not affected during a preparation of external composition for skin, and excellent oxidative stabilities can be achieved in compounds.

Preferred examples of the group represented by the formula (2) include a phenyl group, a 4-methoxyphenyl group, a 3-methoxyphenyl group, a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 2,3,4-trimethoxyphenyl group, a 2,3,5-trimethoxyphenyl group, a 2,3,6-trimethoxyphenyl group, a 2,4,5-trimethoxyphenyl group, a 2,4,6-trimethoxyphenyl group, a 3,4,5-trimethoxyphenyl group, a benzyl group, a p-anisoyl(4-methoxybenzoyl) group, a m-anisoyl(3-methoxybenzoyl) group, an o-anisoyl(2-methoxybenzoyl) group, a 2,3-dimethoxybenzoyl group, a 2,4-dimethoxybenzoyl group, a 2,5-dimethoxybenzoyl group, a 2,6-dimethoxybenzoyl group, a 3,4-dimethoxybenzoyl group, a 3,5-dimethoxybenzoyl group, a 2,3,4-trimethoxybenzoyl group, a 2,3,5-trimethoxybenzoyl group, a 2,3,6-trimethoxybenzoyl group, a 2,4,5-trimethoxybenzoyl group, a 2,4,6-trimethoxybenzoyl group, a 3,4,5-trimethoxybenzoyl group, a phenylacetyl group, a benzenesulfonyl group, a 2-methoxybenzenesulfonyl group, a 3-methoxybenzenesulfonyl group, a 4-methoxybenzenesulfonyl group, a 2,3-dimethoxybenzenesulfonyl group, a 2,4-dimethoxybenzenesulfonyl group, a 2,5-dimethoxybenzenesulfonyl group, a 2,6-dimethoxybenzenesulfonyl group, a 3,4-dimethoxybenzenesulfonyl group, a 3,5-dimethoxybenzenesulfonyl group, a 2,3,4-trimethoxybenzenesulfonyl group, a 2,3,5-trimethoxybenzenesulfonyl group, a 2,3,6-trimethoxybenzenesulfonyl group, a 2,4,5-trimethoxybenzenesulfonyl group, a 2,4,6-trimethoxybenzenesulfonyl group, and a 3,4,5-trimethoxybenzenesulfonyl group.

For a reason of availability, more preferred examples of the group represented by the formula (2) include a phenyl group, a 4-methoxyphenyl group, a 3-methoxyphenyl group, a 2,4-dimethoxyphenyl group, a 3,4-dimethoxyphenyl group, a 3,4,5-trimethoxyphenyl group, a benzyl group, a p-anisoyl(4-methoxybenzoyl) group, a m-anisoyl(3-methoxybenzoyl) group, an o-anisoyl(2-methoxybenzoyl) group, a 2,4-dimethoxybenzoyl group, a 3,4-dimethoxybenzoyl group, a 3,4,5-trimethoxybenzoyl group, a phenylacetyl group, a benzenesulfonyl group, a 2-methoxybenzenesulfonyl group, a 3-methoxybenzenesulfonyl group, a 4-methoxybenzenesulfonyl group, and a 3,4,5-trimethoxybenzenesulfonyl group. The most preferred examples of the group represented by the formula (2) include a phenyl group, a benzyl group, a benzoyl group, a phenylacetyl group or a benzenesulfonyl group.

Preferred examples of the formula (1) corresponding to the above-mentioned groups include N-phenyl gamma-aminobutyric acid, N-4'-methoxyphenyl gamma-aminobutyric acid, N-3'-methoxyphenyl gamma-aminobutyric acid, N-2'-methoxyphenyl gamma-aminobutyric acid, N-2',4'-dimethoxyphenyl gamma-aminobutyric acid, N-3',4'-dimethoxyphenyl gamma-aminobutyric acid, N-3',4',5'-trimethoxyphenyl gamma-aminobutyric acid, N-benzyl gamma-aminobutyric acid, N-benzoyl gamma-aminobutyric acid, N-p-anisoyl gamma-aminobutyric acid, N-m-anisoyl gamma-aminobutyric acid, N-o-anisoyl gamma-aminobutyric acid, N-2',4'-dimethoxybenzoyl gamma-aminobutyric acid, N-3',4'-dimethoxybenzoyl gamma-aminobutyric acid, N-3',4',5'-trimethoxybenzoyl gamma-aminobutyric acid, N-phenylacetyl gamma-aminobutyric acid, N-benzenesulfonyl gamma-aminobutyric acid, N-4'-methoxybenzenesulfonyl gamma-aminobutyric acid, N-3'-methoxybenzenesulfonyl gamma-aminobutyric acid, N-2'-methoxybenzenesulfonyl gamma-aminobutyric acid, N-2',4'-dimethoxybenzenesulfonyl gamma-aminobutyric acid, N-3',4'-dimethoxybenzenesulfonyl gamma-aminobutyric acid, N-3',4',5'-trimethoxybenzenesulfonyl gamma-aminobutyric acid, and N-methyl forms thereof. More preferred examples of the formula (1) include N-phenyl gamma-aminobutyric acid, N-methyl-N-phenyl gamma-aminobutyric acid, N-benzyl gamma-aminobutyric acid, N-methyl-N-benzyl gamma-aminobutyric acid, N-benzoyl gamma-aminobutyric acid, N-phenylacetyl gamma-aminobutyric acid, and N-benzenesulfonyl gamma-aminobutyric acid.

$R_1$ and $R_2$ may jointly form a piperidine ring, morpholine ring, or pyrrolidine ring. The formed piperidine ring, morpholine ring, or pyrrolidine ring may have substituents. However, in view of the effect of substituents on solubility, it is preferred that the ring has no substituent or the substituent is within a range of an alkyl group having 1 to 3 carbon atoms or a hydrogen group.

Preferred examples of formula (1) corresponding to the above-mentioned rings include 4-(1'-piperidine) butyric acid, 4-(1'-morpholine) butyric acid, or 4-(1'-pyrrolidine) butyric acid.

In the present invention, the gamma-aminobutyric acid derivatives are preferably one or more compounds selected from the group consisting of N,N,N-trimethyl gamma-aminobutyric acid, N-methyl gamma-aminobutyric acid, N—N-dimethyl gamma-aminobutyric acid, N-benzyloxycarbonyl gamma-aminobutyric acid, N-cyclohexyl gamma-aminobutyric acid, N-cyclohexyl-N-methyl gamma-aminobutyric acid, N-cyclohexanemethyl gamma-aminobutyric acid, N-cyclohexanemethyl-N-methyl gamma-aminobutyric acid, N-cyclohexanecarbonyl gamma-aminobutyric acid, 4-guanidino butyric acid, 4-ureido butyric acid, N-phenyl gamma-aminobutyric acid, N-phenyl-N-methyl gamma-aminobutyric acid, N-benzyl gamma-aminobutyric acid, N-benzyl-N-methyl gamma-aminobutyric acid, N-benzoyl gamma-aminobutyric acid, N-phenylacetyl gamma-aminobutyric acid, N-benzenesulfonyl gamma-aminobutyric acid, 4-(1'-piperidine) butyric acid, 4-(1'-morpholine) butyric acid, 4-(1'-pyrrolidine) butyric acid, and salts thereof. When the above-mentioned derivatives and salts thereof are used, the best effects of preventing and alleviating wrinkles, a good solubility in preparations, and no problems in safety such as sensory stimulus can be achieved. Thus, the above-mentioned gamma-aminobutyric acid derivatives are most excellent in achieving the object of the present invention.

The gamma-aminobutyric acid derivatives and salts thereof according to the present invention can be obtained by a known synthesis method or an extraction and purification from animals, plants or microorganisms. When especially 4-guanidino butyric acid is used as the gamma-aminobutyric acid derivative and salt thereof, the compound is a known material and available from, for example, Sigma-Aldrich. When any of N-methyl gamma-aminobutyric acid hydrochloride, N-dimethyl gamma-aminobutyric acid hydrochloride, and N-trimethyl gamma-aminobutyric acid hydrochloride ((3-carboxypropyl)trimethylammonium chloride) is used, all of them are known materials and available from, for example, Sigma-Aldrich.

Representative synthetic examples for the gamma-aminobutyric acid derivatives according to the present invention are presented below, however, the present invention is not limited by these examples.

SYNTHETIC EXAMPLE (1) N-benzoyl-gamma-aminobutyric acid 6.4 g of gamma-aminobutyric acid and 4.5 g of sodium hydroxide were dissolved in 100 mL of purified water, and 7.9 g of benzoyl chloride was dropwise added thereto under ice-cooling. After stirring the mixture for 6 hours, hydrochloric acid was added to adjust the pH to 2 or less. The precipitated crude product was filtered, and then recrystallized with ethanol solution to give 8.7 g of the desired product.

(2) N-4'-methoxybenzoyl-gamma-aminobutyric acid

The desired product was obtained with the same components and method as Synthetic example (1), except p-anisoyl chloride was substituted for the benzoyl chloride.

(3) N-3'-methoxybenzoyl-gamma-aminobutyric acid

The desired product was obtained with the same components and method as Synthetic example (1), except m-anisoyl chloride was substituted for the benzoyl chloride.

(4) N-2'-methoxybenzoyl-gamma-aminobutyric acid

The desired product was obtained with the same components and method as Synthetic example (1), except o-anisoyl chloride was substituted for the benzoyl chloride.

(5) N-phenylacetyl-gamma-aminobutyric acid

The desired product was obtained with the same components and method as Synthetic example (1), except phenylacetyl chloride was substituted for the benzoyl chloride.

(6) N-cyclohexanecarbonyl-gamma-aminobutyric acid

The desired product was obtained with the same components and method as Synthetic example (1), except cyclohexanecarbonyl chloride was substituted for the benzoyl chloride.

(7) N-benzenesulfonyl-gamma-aminobutyric acid

7 G of gamma-aminobutyric acid was dissolved in 120 mL of 1N sodium hydroxide solution, and 15 g of benzenesulfonyl chloride was dropwise added thereto under ice-cooling. 2N sodium hydroxide solution was added to the mixture to adjust the pH to 9.2 and stirred for 4 hours. The stirred mixture was washed with 50 mL of ethyl acetate, and hydrochloric acid was added thereto to adjust the pH to 2 or less. After extracting with 500 mL of ethyl acetate, this was dried with magnesium sulfate and filtered. After a concentration under

(8) N-4'-methoxybenzenesulfonyl-gamma-aminobutyric acid

The desired product was obtained with the same components and method as Synthetic example (7), except 4-methoxybenzenesulfonyl chloride was substituted for the benzenesulfonyl chloride.

(9) N-3'-methoxybenzenesulfonyl-gamma-aminobutyric acid

The desired product was obtained with the same components and method as Synthetic example (7), except 3-methoxybenzenesulfonyl chloride was substituted for the benzenesulfonyl chloride.

(10) N-2'-methoxybenzenesulfonyl-gamma-aminobutyric acid

The desired product was obtained with the same components and method as Synthetic example (7), except 2-methoxybenzenesulfonyl chloride was substituted for the benzenesulfonyl chloride.

(11) N-cyclohexyl-gamma-aminobutyric acid 7 g of 4-bromobutyric acid ethyl ester and 20 g of cyclohexylamine were added to 50 mL of ethanol, and the mixture was stirred at a room temperature for one week. The stirred mixture was concentrated under reduced pressure and extracted with 200 mL of ethyl acetate. The extracted material was washed with purified water, dried with magnesium sulfate, and then concentrated. The obtained residue was distilled under reduced pressure to give 8.2 g of N-cyclohexyl-gamma-aminobutyric acid ethyl ester. The obtained N-cyclohexyl-gamma-aminobutyric acid ethyl ester was added to sodium hydroxide solution (1.68 g of sodium hydroxide/100 mL of purified water), and THF was added thereto till the mixture became homogeneous. After stirring at room temperature for 3 hours, the mixture was neutralized with DOWEX50W [H+ form] and concentrated under reduced pressure. The obtained residue was recrystallized to give 4.1 g of the desired product.

(12) N-cyclohexyl-N-methyl-gamma-aminobutyric acid 10 g of 4-bromobutyric acid ethyl ester and 15 g of N-cyclohexyl-N-methylamine were added to 40 mL of ethanol, and the mixture was heated to reflux for 2 hours. After air-cooling, the mixture was concentrated under reduced pressure and extracted with 200 mL of ethyl acetate. The extracted material was washed with purified water, dried with magnesium sulfate, and then concentrated. The obtained residue was distilled under reduced pressure to give 10.5 g of N-cyclohexyl-N-methyl-gamma-aminobutyric acid ethyl ester. The obtained N-cyclohexyl-N-methyl-gamma-aminobutyric acid ethyl ester was added to a sodium hydroxide solution (2.4 g of sodium hydroxide/100 mL of purified water), and THF was added thereto until the mixture became homogeneous. After stirring at room temperature for 3 hours, the mixture was neutralized with DOWEX50W [H+ form] and concentrated under reduced pressure. The obtained residue was recrystallized to give 5.2 g of the desired product.

The gamma-aminobutyric acid derivatives of the present invention may be used as salts, however, using as salts is not essential. The kinds of the salts are not limited in particular, and examples of inorganic salt include sodium salt, potassium salt, calcium salt, zinc salt, magnesium salt, ammonium salt, hydrochloride, hydrosulfate, phosphate, and hydrobromate. Examples of organic salt include methylamine salt, pyridine salt, trimethylamine salt, triethanolamine salt, methyl hydrogen sulfate, p-toluenesulfonate, acetate, lactate, maleate, fumarate, oxalate, succinate, tartrate, citrate, betainate/betaine salt, glycinate/glycine salt, serinate/sarine salt, and taurinate/taurine salt, and the salts in the present invention are not limited to the above-mentioned salts. The salts can be obtained by a known method.

As shown hereinbelow, the gamma-aminobutyric acid derivatives and salts thereof according to the present invention (hereinafter referred to as the gamma-aminobutyric acid derivatives) have excellent effects of preventing and alleviating wrinkles, especially graphic wrinkles or linear wrinkles which are formed by decreased barrier function of the skin owing to aging or photo aging. Thus, a composition for preventing and alleviating wrinkles is prepared by including one or more compounds, as active components, selected from the group consisting of the gamma-aminobutyric acid derivatives according to the present invention.

The agent for preventing and alleviating wrinkles is a novel advantageous application of the above-mentioned gamma-aminobutyric acid derivatives according to the present invention. The agent for preventing and alleviating wrinkles has an extremely wide range of application and is applied in various kinds of field such as the cosmetics field including quasi-drugs, the pharmaceutical field, and the food field. Preferably, the agent is blended into external compositions for skin.

Thus, in the present invention, the composition for preventing and alleviating wrinkles which contains one or more compounds selected from the group consisting of the gamma-aminobutyric acid derivatives is also useful as the composition for preventing and alleviating wrinkles, which achieves excellent effects such as preventing and alleviating wrinkles.

When a composition is prepared according to the present invention, the blending amount of one or more compounds selected from the group consisting of the gamma-aminobutyric acid derivatives is preferably 0.01 to 20.0% by mass with respect to the total amount of the composition, more preferably 0.05 to 10.0% by mass. However, the composition can be prepared by including solely one or more compounds selected from the group consisting of the gamma-aminobutyric acid derivatives.

The composition for preventing and alleviating wrinkles according to the present invention can be prepared by a conventional method. Though the composition can be prepared by including solely one or more compounds selected from the group consisting of the gamma-aminobutyric acid derivatives, other components used in external compositions for skin such as cosmetics including quasi drugs, pharmaceuticals, and so on can be blended in the composition, as necessary, so far as the effects of the present invention are not undermined. Examples of the other components (arbitrarily-blended component) include oil, surfactant, powder, coloring agent, water, alcohols, thickening agent, chelating agent, silicones, antioxidant, UV absorber, moisturizer, perfume, various kinds of drug components, preservative, pH adjuster, and neutralizer.

The composition for preventing and alleviating wrinkles is used in product forms such as cosmetics compositions and pharmaceutical compositions and achieves excellent effects of preventing and alleviating wrinkles. It is especially preferred that the composition for preventing and alleviating wrinkles is applied in cosmetics or pharmaceuticals and is used with an administration method of directly applying onto the skin or spraying to the skin in a form of external composition for skin, resulting in achieving excellent effects of preventing and alleviating wrinkles.

The composition for preventing and alleviating wrinkles of the present invention is applied to the skin so that it can be used in a beauty treatment for preventing wrinkle formation and alleviating or removing formed wrinkles. In the beauty treatment, usage and dosage of the composition for preventing and alleviating wrinkles of the present invention are not limited in particular, and they are determined depending on the forms of the composition or wrinkle conditions in the skin to be treated. As a typical dosage, an adequate dose (e.g. 0.1 ml to 1 ml per 1 cm$^2$) of the composition is applied for several times a day (e.g. 1 to 5 times a day). As a typical usage, the composition can be used by rubbing it directly into the skin or by soaking an adequate dose of the composition in a gauze and so on and applying the gauze to the skin.

The form of the composition for preventing and alleviating wrinkles is not limited in particular so far as the effects of the present invention can be achieved, and it can be any form such as solution form, solubilized form, emulsified from, powder-dispersed form, water-oil 2-layered form, water-oil-powder 3-layered form, ointment form, gel form, and aerosol form.

The composition for preventing and alleviating wrinkles is applied in the fields such as the cosmetic field including quasi-drugs and the pharmaceutical field and can take any product forms such as ointment, cream, milky lotion, skin lotion, essence, jelly, gel, pack, mask, and foundation.

EXAMPLES

Hereinafter, the present invention will be described in further detail with reference to examples. However, the present invention is not limited by these examples. An amount is represented as mass % unless otherwise specified.

In normal skin, nuclei are lost in the terminal process of differentiation which is a transition phase from granular layer to cornified layer, which is called "denucleation". If this "denucleation" does not occur owing to any cause, epidermal keratinocytes in a state of having nuclei are formed, resulting in decreased barrier function of the skin. According to the findings made by the present inventors, it was found that Caspase 14 causes normal denucleation by inducing degradation of ICAD and Serpin b3 inhibits the activation of Caspase 14. Decreased barrier function of the skin, which is evaluated by Transepidermal Water Loss (TEWL) as an indication, shows a strong correlation with expression level of Serpin b3. So, the present inventors have initially investigated an effect that the gamma-aminobutyric acid derivatives of the present invention suppress SCCA 1 (Serpin 3b) expression.

Effect of Suppressing SCCA 1 Expression

Figure 1:
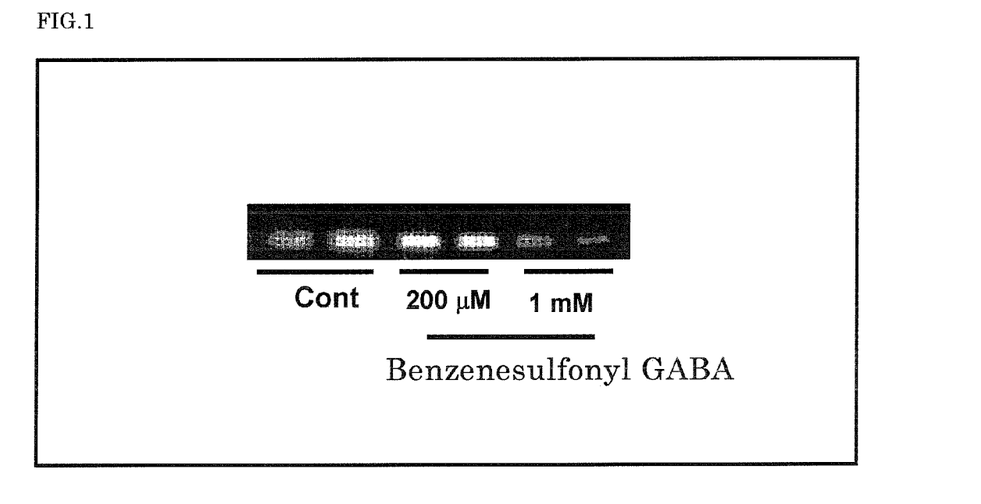
FIG. 1 shows the results of measuring the SCCA 1 expression level in the samples to which 200 μM and 1 mM of N-benzenesulfonyl-gamma-aminobutyric acid are respectively added. (Control sample: No addition of aminobutyric acid derivatives).

Human normal keratinocytes (manufactured by KURABO INDUSTRIES LTD.) were incubated with culture medium, Epilife (manufactured by KURABO INDUSTRIES LTD.) For medium replacement, the medium was subcultured for three times a week. The human normal keratinocytes were seeded on 3.5 cm dishes. In the phase of 60 to 70% confluent, 200 μM and 1 mM of N-benzenesulfonyl-gamma-aminobutyric were respectively added to the dishes, which were incubated for 24 hours. Then RNAs were extracted with use of Isogen, and SCCA 1 (Serpin b3) expression levels were measured by RT-PCR. Additionally, as a control sample, the same test except no addition of gamma-aminobutyric acid derivatives was conducted. G3PDH was used as internal standard. The primers used for PCR were as follows. The result is shown in FIG. 1.

```
human SCCA1 forward primer
                                (SEQ ID NO: 1)
5'-GTGCTATCTGGAGTCCT-3';

reverse primer
                                (SEQ ID NO: 2)
5'-CTGTTGTTGCCAGCAA-3';

human G3PDH forward primer
                                (SEQ ID NO: 3)
5'-GAAGGTGAAGGTCGGAGTC-3'; and reverse primer
                                (SEQ ID NO: 4)
5'-GAAGATGGTGATGGGATTTC-3'.
```

As shown in FIG. 1, it was revealed that, in the samples to which 200 μM and 1 mM of N-benzenesulfonyl-gamma-aminobutyric acid were respectively added, Serpin b3 expression levels was significantly decreased depend on the additive amount of N-benzenesulfonyl-gamma-aminobutyric acid, compared with the control sample to which no gamma-aminobutyric acid derivatives were added.

According to the aforementioned results, it is considered that the gamma-aminobutyric acid derivatives of the present invention inhibit Serpin b3 expression, which relates to decreased barrier function of the skin, and allows normal denucleation to occur easily in the skin, resulting in inhibiting decreased barrier function of the skin.

The present inventors have subsequently conducted an actual use test in human so as to further investigate the alleviating effect of the gamma-aminobutyric acid derivatives of the present invention on wrinkles.

Test for an Effect of Alleviating Wrinkles in the Outer Corner of Human's Eye

Thirty healthy adults having wrinkles in the outer corners of eyes, between the age of 30 and 60 (average age: 46 years old), applied a solution which contained the agent for preventing and alleviating wrinkles (Example 1) to the outer corner of one eye and another solution which did not contain the agent for preventing and alleviating wrinkles (Comparative example 1) to the outer corner of the other eye every day. Each solution was applied three times a day for one month. The replicas of their wrinkles before and after applying each solution were collected with use of SILFLO (a material for making replica, manufactured by Amique Group Co., Ltd.). The collected replicas were analyzed with a 3D wrinkle analyzer (refer to Japanese Unexamined Patent Publication 7-116146 for an analyzer for analyzing wrinkles and a method thereof).

| (Component) | Amount (mass %) |
|---|---|
| Composition of Example 1 | |
| N-benzenesulfonyl-gamma-aminobutyric acid | 1.0 |
| Ethanol for cosmetic use | 15.0 |
| Purified water | Balance |
| Composition of Comparative example 1 | |
| Ethanol for cosmetic use | 15.0 |
| Purified water | Balance |

Figure 2:
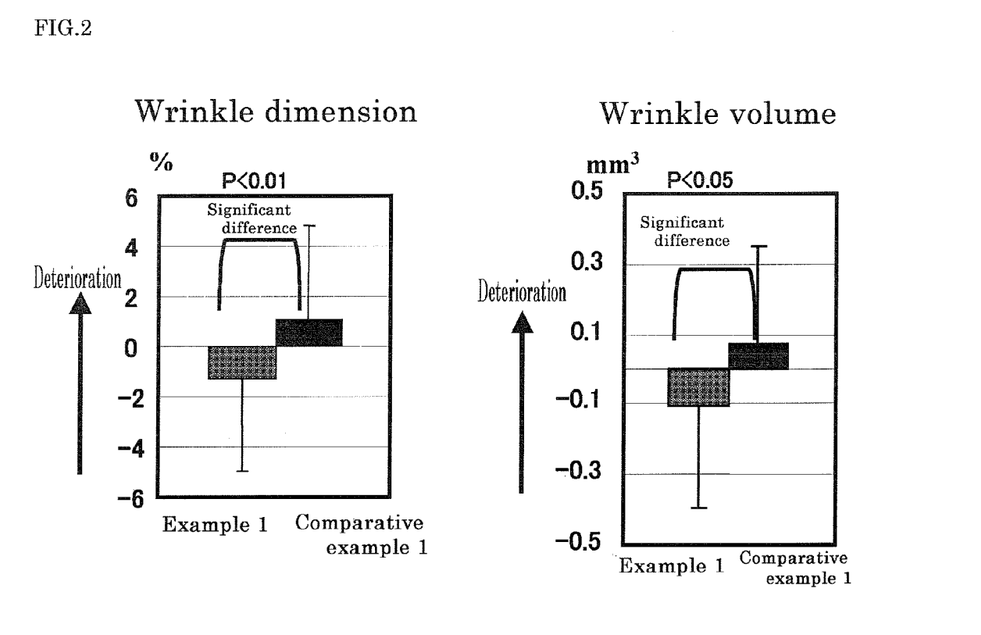
FIG. 2 are the graphs showing variations in wrinkle dimension and in wrinkle volume, before and after applying a solution which contains N-benzenesulfonyl-gamma-aminobutyric acid (Example 1) and a solution which does not contain aminobutyric acid derivatives (Comparative example 1).

FIG. 2 shows the results of calculating wrinkle dimensions and wrinkle volumes per 1 cm$^2$ by 3D-analyzing the replicas of the outer corners of eyes. For the wrinkle dimension (the wrinkle volume), a variation after applying each solution for one month is calculated based on the wrinkle dimension (the wrinkle volume) before starting the test.

As shown in FIG. 2, the wrinkle dimension was decreased by applying Example 1 though the application of Comparative example 1 did not inhibit the wrinkle dimension from increasing. In the same way, the wrinkle volume was decreased by applying Example 1 though it was increased by applying Comparative example 1.

In addition, when the variation of wrinkle dimension before and after applying Example 1 was compared with the variation of wrinkle dimension before and after applying Comparative example 1 and statistically analyzed with use of Student's t-test, it was found that Example 1 had a significant effect of alleviating wrinkles. In the same way, when statistical analysis was conducted with use of Student's t-test in the variations of wrinkle volumes before and after applying each example, it was found that Example 1 had a significant effect of alleviating wrinkles.

As a summary of the aforementioned test results, it is understood that the gamma-aminobutyric acid derivatives of the present invention prevent decreased barrier function of the skin by inhibiting epidermal SCCA expression, which prevents wrinkle formation or significantly alleviates formed wrinkles. Thus, the gamma-aminobutyric acid derivatives and salts thereof of the present invention have excellent effects of preventing and alleviating graphic wrinkles and linear wrinkles which are formed by decreased barrier function of the skin owing to aging or photo aging.

The formulation examples of the agent for preventing and alleviating wrinkles according to the present invention are described hereinbelow. All formulation examples had excellent effects of preventing and alleviating wrinkles when they were applied to the skin.

| Formulation example 1: Cream | |
|---|---|
| Stearic acid | 5.0 (mass %) |
| Stearyl alcohol | 4.0 |
| Isopropyl myristate | 18.0 |
| Glyceryl Monostearate | 3.0 |
| Propylene glycol | 10.0 |
| N-benzenesulfonyl-gamma-aminobutyric acid | 20.0 |
| Potassium hydroxide | 0.2 |
| Sodium bisulfite | 0.01 |
| Preservative | Q.S. |
| Perfume | Q.S. |
| Ion-exchanged water | Balance |

(Production Method)

Propylene glycol, Potassium hydroxide, and N-benzenesulfonyl-gamma-aminobutyric acid were added to ion-exchanged water. The mixture was dissolved by heating and maintaining at 70° C. (water phase). The other components were mixed, dissolved by heating, and maintaining at 70° C. (oil phase). The oil phase was gradually added to the water phase. After all of the oil phase was added, they were reacted for a while at the same temperature. Then, the reacted mixture was emulsified homogenously with a homomixer and cooled to 30° C. by mixing it well to obtain the desired cream.

| Formulation example 2: Cream | |
|---|---|
| Stearic acid | 6.0 (mass %) |
| Sorbitan monostearate | 2.0 |
| Polyoxyethylene (20 mol) sorbitan monostearate | 1.5 |
| Propylene glycol | 10.0 |
| N-methyl-gamma-aminobutyric acid | 7.0 |
| Glycerin trioctanoate | 10.0 |
| Squalene | 5.0 |
| Sodium bisulfite | 0.01 |
| Ethyl paraben | 0.3 |
| Perfume | Q.S. |
| Ion-exchanged water | Balance |

(Production Method)

Propylene glycol and N-methyl-gamma-aminobutyric acid were added to ion-exchanged water. The mixture was dissolved by heating and kept to 70° C. (water phase). The other components were mixed, dissolved by heating, and kept to 70° C. (oil phase). The oil phase was added to the water phase and pre-emulsified. The pre-emulsified mixture was emulsified homogenously with a homomixer, and then cooled to 30° C. by mixing it well to obtain the desired cream.

| Formulation example 3: Cream | |
|---|---|
| Stearyl alcohol | 7.0 (mass %) |
| Stearic acid | 2.0 |
| Hydrogenated lanolin | 2.0 |
| Squalane | 5.0 |
| 2-Octyldodecyl alcohol | 6.0 |
| Polyoxyethylene (25 mol) cetyl alcohol ether | 3.0 |
| Glyceryl Monostearate | 2.0 |
| Propylene glycol | 5.0 |
| N-benzoyl-gamma-aminobutyric acid | 0.001 |
| Perfume | Q.S. |
| Sodium bisulfite | 0.03 |
| Ethyl paraben | 0.3 |
| Ion-exchanged water | Balance |

(Production Method)

Propylene glycol was added to ion-exchanged water. The mixture was dissolved by heating and kept to 70° C. (water phase). The other components were mixed, dissolved by heating, and kept to 70° C. (oil phase). The oil phase was added to the water phase and pre-emulsified. The pre-emulsified mixture was emulsified homogenously with a homomixer, and then cooled to 30° C. by mixing it well to obtain the desired cream.

| Formulation example 4: Milky lotion | |
|---|---|
| Stearic acid | 2.5 (mass %) |
| Cetyl alcohol | 1.5 |
| Petrolatum | 5.0 |
| Liquid paraffin | 10.0 |
| Polyoxyethylene (10 mol) monooleate | 2.0 |
| Polyethylene glycol 1500 | 3.0 |
| Triethanolamine | 1.0 |
| N,N,N-trimethyl-gamma-aminobutyric acid | 10.0 |
| Sodium bisulfite | 0.01 |
| Ethyl paraben | 0.3 |
| Carboxyvinyl polymer | 0.05 |
| Perfume | Q.S. |
| Ion-exchanged water | Balance |

(Production Method)

Carboxyvinyl polymer was dissolved in a small amount of ion-exchanged water (phase A). Polyethylene glycol 1500, N,N,N-trimethyl-gamma-aminobutyric acid, and triethanolamine were added to the rest of ion-exchanged water. The mixture was dissolved by heating and maintaining at 70° C.

(water phase). The other components were mixed, dissolved by heating, and maintaining at 70° C. (oil phase). The oil phase was added to the water phase and pre-emulsified. The phase A was added to the pre-emulsified mixture and emulsified homogenously with a homomixer, and then cooled to 30° C. by mixing it well to obtain the desired milky lotion.

| Formulation example 5: Milky lotion | | |
| --- | --- | --- |
| (Oil phase) | | |
| Stearyl alcohol | 1.5 | (mass %) |
| Squalene | 2.0 | |
| Petrolatum | 2.5 | |
| Deodorized-liquid lanolin | 1.5 | |
| Evening primrose oil | 2.0 | |
| Isopropyl myristate | 5.0 | |
| Glycerin monooleate | 2.0 | |
| Polyoxyethylene (60 mol) hydrogenated castor oil | 2.0 | |
| Tocopheryl acetate | 0.05 | |
| Ethyl paraben | 0.2 | |
| Butyl paraben | 0.1 | |
| Ethylglycine | 1.0 | |
| Perfume | Q.S. | |
| (Water phase) | | |
| Sodium bisulfite | 0.01 | |
| N-cyclohexyl-gamma-aminobutyric acid | 1.0 | |
| Glycerin | 5.0 | |
| Sodium hyaluronate | 0.01 | |
| Carboxyvinyl polymer | 0.2 | |
| Potassium hydroxide | 0.2 | |
| Purified water | Balance | |

(Production Method)

The components of the oil phase were dissolved at 70° C. The components of the water phase were dissolved at 70° C. The oil phase was mixed with the water phase. The mixture was emulsified with an emulsification equipment and cooled to 30° C. by a heat exchanger to obtain the desired milky lotion.

| Formulation example 6: Jelly | | |
| --- | --- | --- |
| 95% Ethyl alcohol | 10.0 | (mass %) |
| Dipropylene glycol | 15.0 | |
| Polyoxyethylene (50 mol) oleyl alcohol ether | 2.0 | |
| Carboxyvinyl polymer | 1.0 | |
| Sodium hydroxide | 0.15 | |
| L-arginine | 0.1 | |
| N-benzyloxycarbonyl gamma-aminobutyric acid | 1.0 | |
| Methyl paraben | 0.2 | |
| Perfume | Q.S. | |
| Ion-exchanged water | Balance | |

(Production Method)

Carboxyvinyl polymer was homogenously dissolved in ion-exchanged water. N-benzyloxycarbonyl gamma-aminobutyric acid and polyoxyethylene (50 mol) oleyl alcohol ether were dissolved in 95% ethyl alcohol and added to the water phase. Then, after other components were added thereto, the mixture was neutralized and thickened by sodium hydroxide and L-arginine to obtain the desired jelly.

| Formulation example 7: Essence | | |
| --- | --- | --- |
| (Phase A) | | |
| 95% Ethyl alcohol | 10.0 | (mass %) |
| Polyoxyethylene (20 mol) octyldodecanol | 1.0 | |
| Methyl paraben | 0.15 | |

| Formulation example 7: Essence | |
| --- | --- |
| Pantothenyl ethyl ether | 0.1 |
| N-benzyl gamma-aminobutyric acid | 0.05 |
| (Phase B) | |
| Potassium hydroxide | 0.1 |
| (Phase C) | |
| Glycerin | 5.0 |
| Dipropylene glycol | 10.0 |
| Sodium bisulfite | 0.03 |
| Carboxyvinyl polymer | 0.2 |
| Purified water | Balance |

(Production Method)

Each of phase A and phase C was homogenously dissolved, and phase A was added to phase C to be solubilized. Then, phase B was added to the mixture to obtain the desired essence by filling.

| Formulation example 8: Pack | | |
| --- | --- | --- |
| (Phase A) | | |
| Dipropylene glycol | 5.0 | (mass %) |
| Polyoxyethylene (60 mol) hydrogenated castor oil | 5.0 | |
| (Phase B) | | |
| Olive oil | 5.0 | |
| Tocopheryl acetate | 0.2 | |
| Ethyl paraben | 0.2 | |
| Perfume | 0.2 | |
| (Phase C) | | |
| 4-guanidino butyric acid | 1.0 | |
| N-cyclohexanemethyl gamma-aminobutyric acid | 1.0 | |
| N-cyclohexyl-N-methyl gamma-aminobutyric acid | 0.7 | |
| Sodium bisulfite | 0.03 | |
| Polyvinyl alcohol (Saponification degree: 90, Polymerization degree: 2000) | 13.0 | |
| Ethanol | 7.0 | |
| Purified water | Balance | |

(Production Method)

Each of the phases A, B, and C was homogenously dissolved, and phase B was added to phase A to be solubilized. Then, the mixture was added to phase C to obtain the desired pack.

| Formulation example 9: Ointment | | |
| --- | --- | --- |
| Polyoxyethylene (30 mol) cetyl ether | 2.0 | (mass %) |
| Glycerin monostearate | 10.0 | |
| Liquid paraffin | 10.0 | |
| Petrolatum | 40.0 | |
| Cetanol | 6.0 | |
| Methyl paraben | 0.1 | |
| Butyl paraben | 0.1 | |
| Glyceryl Monostearate | 2.0 | |
| 4-(1'-piperidine) butyric acid | 5.0 | |
| Propylene glycol | 10.0 | |
| Ion-exchanged water | Balance | |
| Perfume | Q.S. | |

(Production Method)

4-(1'-piperidine) butyric acid was added to ion-exchanged water, dissolved by heating, and kept to 70° C. (water phase). The other components were mixed at 70° C. and dissolved (oil phase). The oil phase was added to the water phase, emulsified homogenously with a homomixer, and cooled to obtain the desired ointment.

| Formulation example 10: Cream | Amount (mass %) |
|---|---|
| (1) Liquid paraffin | 8.0 |
| (2) Petrolatum | 3.0 |
| (3) Dimethylpolysiloxane | 2.0 |
| (4) Stearyl alcohol | 3.0 |
| (5) Behenyl alcohol | 2.0 |
| (6) Glycerin | 5.0 |
| (7) Dipropylene glycol | 4.0 |
| (8) Trehalose | 1.0 |
| (9) Pentaerythritol tetra-2-ethylhexanoate | 4.0 |
| (10) Polyoxyethylene glyceryl monoisostearate | 2.0 |
| (11) Polyoxyethylene glyceryl monostearate | 1.0 |
| (12) Lipophilic glyceryl monostearate | 2.0 |
| (13) Citric acid | 0.05 |
| (14) Sodium citrate | 0.05 |
| (15) Potassium hydroxide | 0.015 |
| (16) Oil-soluble glycyrrhiza glabra extract | 0.1 |
| (17) Retinol palmitate (megaunit) | 0.25 |
| (18) 4-ureido butyric acid | 1.0 |
| (19) Tocopheryl acetate | 0.1 |
| (20) P-hydroxybenzoic ester | Q.S. |
| (21) Phenoxyethanol | Q.S. |
| (22) Dibutylhydroxytoluene | Q.S. |
| (23) Trisodium edetate | 0.05 |
| (24) 4-t-butyl-4'-methoxybenzoylmethane | 0.01 |
| (25) 2-ethylhexyl p-methoxycinnamate | 0.1 |
| (26) Beta-carotene | 0.01 |
| (27) Polyvinyl alcohol | 0.5 |
| (28) Hydroxyethyl cellulose | 0.5 |
| (29) Carboxyvinyl polymer | 0.05 |
| (30) Purified water | Balance |
| (31) Perfume | Q.S. |

(Production Method)

(27) to (29) were dissolved in (30), and then (6) to (8), (13), (14), (18), (21), and (23) to (25) were added thereto. The mixture was heated to 70° C., and the temperature was retained (water phase). (1) to (5), (9) to (12), (16), (17), (19), (20), (22), (26), and (31) were mixed and dissolved (oil phase). The oil phase was added to the water phase, mixed homogenously, and neutralized by adding (15). Then, the product was prepared by cooling and filling.

| Formulation example 11: Cream | Amount (mass %) |
|---|---|
| (1) Petrolatum | 2.0 |
| (2) Dimethylpolysiloxane | 2.0 |
| (3) Ethanol | 5.0 |
| (4) Behenyl alcohol | 0.5 |
| (5) Batylalcohol | 0.2 |
| (6) Glycerin | 7.0 |
| (7) 1,3-butylene glycol | 5.0 |
| (8) Polyethylene glycol 20000 | 0.5 |
| (9) Jojoba oil | 3.0 |
| (10) Squalane | 2.0 |
| (11) Phytosteryl hydroxystearate | 0.5 |
| (12) Pentaerythritol tetra-2-ethylhexanoate | 1.0 |
| (13) Polyoxyethylene hydrogenated castor oil | 1.0 |
| (14) Potassium hydroxide | 0.1 |
| (15) Sodium pyrosulfite | 0.01 |
| (16) Sodium hexametaphosphate | 0.05 |
| (17) Stearyl glycyrrhetate | 0.1 |
| (18) Pantothenyl ethyl ether | 0.1 |
| (19) Arbutin | 7.0 |
| (20) Tranexamic acid methylamide hydrochloride | 1.0 |
| (21) 4-(1'-morpholine) butyric acid | 1.0 |
| (22) Tocopheryl acetate | 0.1 |
| (23) Sodium hyaluronnate | 0.05 |
| (24) P-hydroxybenzoic ester | Q.S. |
| (25) Trisodium edetate | 0.05 |
| (26) 4-t-butyl-4'-methoxybenzoylmethane | 0.1 |
| (27) Glyceryl di(p-methoxycinnamate) mono(2-ethylhexanoate) | 0.1 |
| (28) Iron oxide yellow | Q.S. |
| (29) Xanthan Gum | 0.1 |
| (30) Carboxyvinyl polymer | 0.2 |
| (31) Purified water | Balance |

(Production Method)

(29) and (30) were dissolved in (31), and then (3), (6) to (8), (15), (16), (18) to (21), and (23) were added thereto. The mixture was heated to 70° C., and the temperature was retained (water phase). (1), (2), (4), (5), (9) to (13), (17), (22), (24), (26), and (27) were mixed and dissolved (oil phase). (25) and (28) were added to a small amount of (31) and dispersed by a homomixer (color agent). The oil phase and the color agent were added to the water phase, mixed homogenously, and neutralized by adding (14). Then, the product was prepared by cooling and filling.

Formulation Example 12

Cream

A cream for alleviating wrinkles of the formulation example 12 was prepared by the same formulation and production method as the formulation example 11, except 4-(1'-pyrrolidine) butyric acid was substituted for the 4-(1'-morpholine) butyric acid.

Formulation Example 13

Cream

A cream for alleviating wrinkles of the formulation example 13 was prepared by the same formulation a-aminobutyric acid was substituted for the 4-(1'-morpholine) butyric acid.

What is claimed is:

1. A method of alleviating graphic wrinkles or linear wrinkles resulting from decreased barrier function of skin comprising:
applying to the skin of a human in need of alleviating graphic or linear wrinkles resulting from decreased barrier function of skin one or more compounds selected from the group consisting of N-benzenesulfonyl gamma-aminobutyric acid and salts thereof.

2. The method according to claim 1 wherein the one or more compounds selected from the group consisting of N-benzenesulfonyl gamma-aminobutyric acid and salts thereof are applied to the skin in a composition, and wherein the composition includes 0.01 to 20.0 mass % of the one or more compounds selected from the group consisting of N-benzenesulfonyl gamma-aminobutyric acid and salts thereof.

3. A method of alleviating wrinkles resulting from squamous cell carcinoma antigen 1 (SCCA1) expression on skin comprising:
applying to the skin of a human in need of alleviating wrinkles resulting from SCCA1 expression one or more compounds selected from the group consisting of N-benzenesulfonyl gamma-aminobutyric acid and salts thereof.

4. The method according to claim 3 wherein the one or more compounds selected from the group consisting of N-benzenesulfonyl gamma-aminobutyric acid and salts thereof are applied to the skin in a composition, and wherein the composition includes 0.01 to 20.0 mass % of the one or more compounds selected from the group consisting of N-benzenesulfonyl gamma-aminobutyric acid and salts thereof.

* * * * *